United States Patent [19]
Yamaguchi et al.

[11] Patent Number: 4,828,997
[45] Date of Patent: May 9, 1989

[54] APPARATUS AND PROCESS FOR PRODUCING GEL BEADS OF MICROBIAL CELLS OR ENZYMES

[75] Inventors: Tetsuo Yamaguchi; Setsuo Saitou; Toshimi Mukushi, all of Hitachi, Japan

[73] Assignee: Hitachi, Ltd., Tokyo, Japan

[21] Appl. No.: 900,418

[22] Filed: Aug. 26, 1986

[30] Foreign Application Priority Data

Aug. 30, 1985 [JP] Japan .................. 60-189648

[51] Int. Cl.⁴ .................. C12N 11/00; C12N 11/02; C12N 11/04; C12M 1/40
[52] U.S. Cl. .................. 435/178; 435/177; 435/182; 435/288
[58] Field of Search .............. 435/177, 178, 182, 288; 34/59; 264/4, 8; 366/293, 295

[56] References Cited

U.S. PATENT DOCUMENTS

| | | | |
|---|---|---|---|
| 2,953,359 | 9/1960 | Mau | 366/295 X |
| 3,499,745 | 3/1970 | Plumat | 264/8 |
| 3,871,111 | 3/1975 | Porr | 34/59 X |
| 4,218,409 | 8/1980 | Donnelly | 264/4 |
| 4,386,895 | 6/1983 | Sodickson | 264/4 X |
| 4,391,909 | 7/1983 | Lim | 435/182 X |
| 4,613,076 | 9/1986 | Dietz et al. | 264/8 X |

Primary Examiner—David M. Naff
Attorney, Agent, or Firm—Antonelli, Terry & Wands

[57] ABSTRACT

Gel beads of microbial cells or enzymes enclosed in gels are produced by forming a surface liquid stream of a gelling agent flowing from the center toward the peripheral wall of a vessel containing the gelling agent by a lower rotor on the liquid surface of the gelling agent, and dispersing a colloidal suspension of microbial cells or enzymes into a droplets by an upper rotor and allowing the dispersed droplets to fall onto the surface liquid stream, thereby contacting the droplets with the gelling agent. The lower and upper rotors may have vanes radially provided at a periphery of a lower and upper sides, respectively. In place of separate rotors, a single rotor may be used with lower and upper surfaces which respectively provide the functions of the lower and upper rotors. The lower and upper surfaces may also have radially provided vanes. The lower and upper rotors or the lower and upper surfaces of a single rotor are spaced sufficiently from each other so that gelling agent is not splashed by the lower rotor or surface onto the upper rotor at surface. The bead size of gel beads can be adjusted by adjusting the number of revolutions of the rotor, and gel beads of smaller bead size can be produced in a mass production scale without any problem of nozzle clogging and without using a number of nozzles of smaller size.

17 Claims, 4 Drawing Sheets

APPARATUS AND PROCESS FOR PRODUCING GEL BEADS OF MICROBIAL CELLS OR ENZYMES

BACKGROUND OF THE INVENTION

This invention relates to a novel apparatus and a novel process for producing gel beads of microbial cells or enzyme, particularly gel beads of microbial cells or enzyme enclosed in gels.

A technique of producing gel beads of microbial cells or enzyme by suspending microbial cells or enzyme in a colloidal solution such as an alginate solution, a carrageenan solution, etc., dispersing the colloidal suspension into a droplet state, and contacting the droplets of the colloidal suspension with a gelling agent such as an aqueous calcium chloride solution or an aqueous potassium chloride solution has been so far widely utilized in the production of gel beads of immobilized microbial cells or immobilized enzyme by gel enclosure.

Heretofore, dispersion of a colloidal suspension of microbial cells or enzyme in a colloidal solution, which will be hereinafter referred to merely as "colloidal suspension", into a droplet state and contacting of the droplets of the colloidal suspension with a gelling agent are carried out according to a nozzle trickling method. However, the nozzle tricking method has such problems as larger sizes of produced gel beads and restriction to the capacity to produce gel beads. An improvement of the nozzle tricking method is proposed in Japanese Patent Application Kokai (Laid-Open) No. 57-186446. The proposed improvement is to provide an air purging around a trickling nozzle for a colloidal suspension, where an increased capacity to produce the gel beads can be expected. However, a large number of nozzles are required for increasing the capacity to produce the gel beads and also it is necessary to supply a sterilized air as the purging air. Thus, the structure and operation are complicated. Furthermore, to produce gel beads of smaller bead size, it is necessary to use nozzles of smaller size. Such nozzles are liable to be clogged and mass production cannot be assured.

On the other hand, a method for forming uniform droplets by breaking up a jet stream of a colloidal suspension, using a resonance technique, is proposed [Biotechnology and Bioengineering, 27, June (1985), 870–876]. However, the proposed method requires a special device for resonance and is not suitable for mass production of gel beads.

SUMMARY OF THE INVENTION

An object of the present invention is to provide an apparatus and a process for producing gel beads of microbial cells or enzyme enclosed in gels with small bead sizes in a mass production scale without any clogging problem in the technique of dispersing a colloidal suspension of microbial cells or enzyme in a colloidal solution such as an alginate solution, a carrageenan solution, etc. into a droplet state, and contacting the droplets of the colloidal suspension with a gelling agent such as an aqueous calcium chloride solution, an aqueous potassium chloride solution, etc., thereby forming gel beads.

According to the present invention, there is provided an apparatus for producing gel beads of microbial cells or enzyme enclosed in gels, which comprises a vessel containing a liquid gelling agent; a lower rotor and an upper rotor being provided coaxially at two stages at the center in the cross-section of the vessel and rotatable by a rotary means, the lower rotor being provided at a level in contact with the liquid surface of the gelling agent contained in the vessel; and a feed pipe for supplying a colloidal suspension of microbial cells or enzyme in a colloidal solution being provided above the upper rotor and having an opening at a position near the center of the upper rotor, and there is also provided a process for producing gel beads of microbial cells or enzyme enclosed in gels, which comprises rotating an upper rotor and a coaxial lower rotor in a vessel containing a gelling agent, a coaxial lower rotor being in contact with the liquid surface of the gelling agent, thereby forming a surface liquid stream of the gelling agent flowing from the center toward the periphery of the vessel, feeding a colloidal suspension of microbial cells or enzyme in a colloidal solution onto the upper side of coaxially rotating upper rotor, dispersing the colloidal suspension into a droplet state by rotation of the upper rotor, and allowing the droplets of the colloidal suspension onto the surface liquid stream of the gelling agent contained in the vessel, thereby forming gel beads.

The lower rotor comprises a disk and vanes radially provided at the periphery on the lower side of the disk. The upper rotor comprises a disk and vanes radially provided at the periphery on the upper side of the disk.

The mechanism of rotating a rotor, supplying a liquid onto the rotating rotor, and dispersing the liquid into droplets seems to be similar to that of a conventional spray drier of rotating disk type. However, the present apparatus is quite different from the spray drier in the structure and the function. That is, in the present invention, a gelling agent is placed in a vessel provided with a lower rotor and an upper rotor coaxially at two stage, and a colloidal suspension of microbial cells or enzyme in a colloid solution is dispersed into a droplet state by rotation of the upper rotor, and at the same time a surface liquid stream of the gelling agent is formed to flow from the center toward the peripheral wall of the vessel on the surface of the gelling agent by rotation of the lower rotor.

In the conventional spray drier of rotating disk type, on the other hand, a liquid is dispersed into a droplet state by a rotating disk distributor and at the same time hot air is supplied into the spray drier and allowed to contact the dispersed droplets. The liquid is evaporated from the droplets, and the dried residues are produced and recovered as particles. Even if a gelling agent is placed in the vessel of the spray drier and a colloidal suspension of microbial cells or enzyme in a colloid solution is dispersed into a droplet state by the rotating disk distributor of the spray drier, it is quite difficult to obtain gel beads of appropriate shape, because in the spray drier any movement of the gelling agent from the center toward the peripheral wall of the vessel cannot be expected on the liquid surface of the gelling agent by rotation of the disk distributor, and the droplets dispersed by the disk distributor stays on the liquid surface of the gelling agent and join with the successively dispersed droplets. Even if the distributor of the spray drier is provided at a level in contact with the liquid surface of the gelling agent in the spray drier, and formation of a surface liquid stream of the gelling agent and dispersion of droplets of the colloidal suspension into a droplet state are carried out at the same time by rotation of the disk distributor, it is quite difficult to obtain gel beads of an appropriate shape, because the formation of a surface liquid stream of the gelling agent and the distribution of the colloidal suspension into a droplet state are carried out by a single thin rotor, i.e. single disk distributor, and thus the colloidal suspension contacts the gelling agent at the peripheral edge of the rotor and undergoes gelling at the edge.

The present invention is thus quite different from the conventional spray drier of rotary disk distributor type in the structure and the function.

PREFERRED EMBODIMENTS OF THE INVENTION

Figure 1:
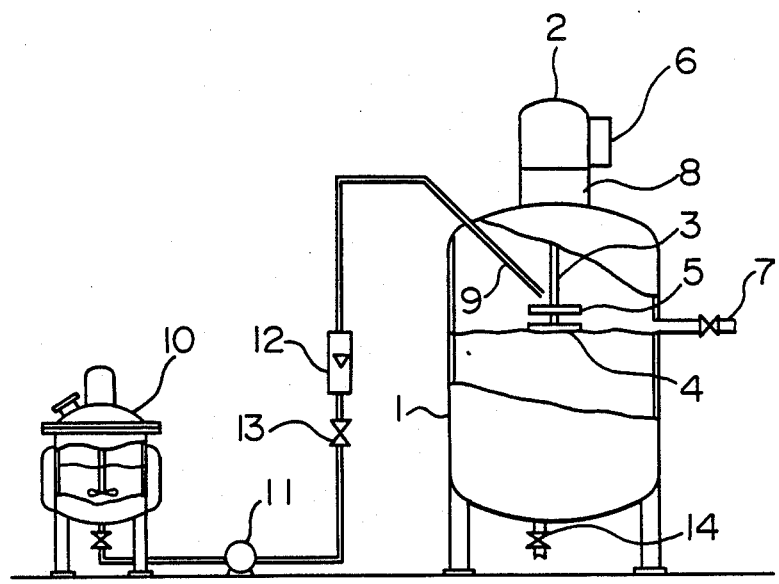
FIG. 1 is a schematic view of an apparatus for producing gell beads of microbial cells or enzyme enclosed in gells according to the present invention.

One embodiment of the present invention will be described, referring to FIG. 1.

A rotating means, for example, a motor 2, is provided at the top of a cylindrical vessel 1 containing a predetermined amount of a gelling agent to rotate a lower rotor 4 and an upper rotor 5 fixed to a rotating shaft 3 vertically provided at the center of the vessel 1 through a transmission means (not shown in the drawing). To set the lower roto 4 and the upper rotor 5 to an appropriate rpm, an rpm-adusting means 6 is provided on the motor 2 or on the transmission means. The diameter of the vessel 1 is selected to such a minimum size that the droplets of a colloidal suspension of microbial cells or enzyme in a colloid solution, fed onto the upper side of the upper rotor 5 and scattered by rotation of the upper rotor 5 may not attach to the peripheral wall of the vessel 1.

To appropriately adjust the contact state of the liquid surface of the gelling agent contained in the vessel 1 with the lower rotor 4, a liquid discharge pipe 7 is provided at an appropriate level at the side wall of the vessel 1. A screen such as wiremesh, etc. is provided at the opening of the liquid discharge pipe 7 to prevent the formed gell beads from discharging through the liquid discharge pipe 7. Furthermore, to make minute adjustment of the contact state of the liquid surface of the gelling agent contained in the vessel 1 with the lower rotor 4, a means 8 for vertically moving the rotating shaft 3, which can move the lower rotor 4 through the shaft 3, is provided.

Figure 2:
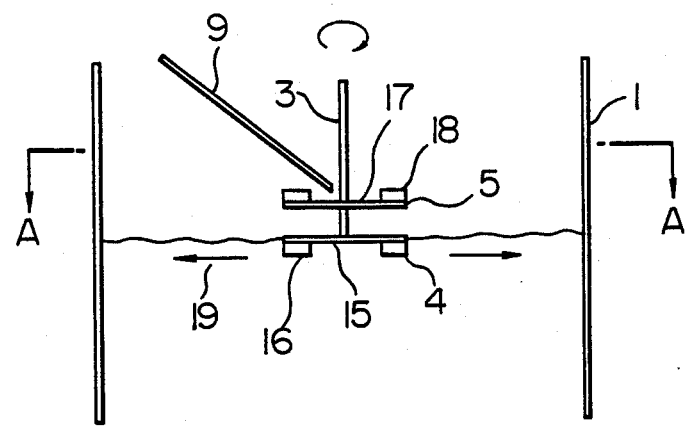
FIG. 2 is a schematic view of a lower rotor and an upper rotor according to the present invention.

The contact state of the liquid surface of the gelling agent with the lower rotor 4 is provided at such a level that a surface liquid stream flowing from the center toward the peripheral wall of the vessel 1 can be obtained by rotation of the lower rotor 4 without any deposition of splashes of the gelling agent onto the upper rotor 5 by the rotation and with a low consumption power. Thus, the dipping depth of the lower rotor 4 in the gelling agent is important, and is thus adjusted by the liquid discharge pipe 7 and the means 8 for vertically moving the rotating shaft. The lower rotor 4 makes a surface liquid stream flow from the center toward the peripheral wall of the vessel 1 on the liquid surface of the gelling agent contained in the vessel 1 by its rotation without deposition of splashes of the gelling agent onto the upper rotor 5. According to one specific embodiment, the lower rotor 4 comprises a disk 15 and vanes 16 radially provided at the periphery on the lower side of the disk 15, as shown in FIG. 2.

Figure 3:
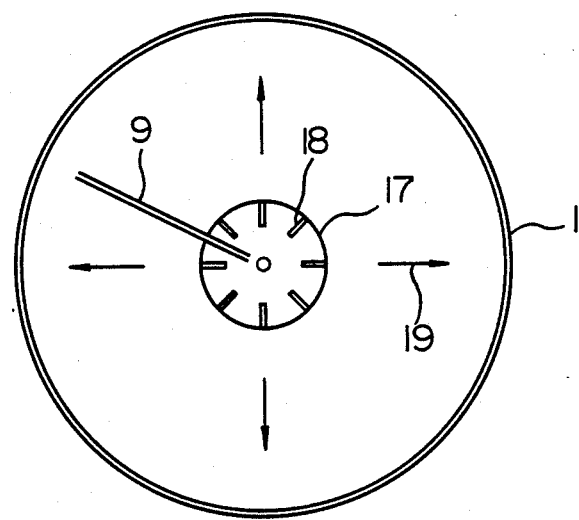
FIG. 3 is a plan view along the line A—A of FIG. 2.

The upper rotor 5 disperses a colloidal suspension supplied to the upper side of the upper rotor 5 into appropriate droplets by its rotation. According to one specific embodiment, the upper rotor 5 comprises a disk 17 and vanes 18 radially provided at the periphery on the upper side of the disk 17, as shown in FIG. 3.

The diameters of the lower disk 4 and the upper disk 5 are selected in accordance with the amount of the colloidal suspension to be treated. The distance between the lower rotor 4 and the upper rotor 5 must be such a minimum distance that the splashes of the gelling agent scattered by rotation of the lower rotor 4 may not attach to the upper rotor.

A feed pipe 9 for the colloidal suspension is provided at a position near the rotating shaft 3 on the upper side of the disk 17 of the upper rotor 5, so that the outlet of the feed pipe 9 can be positioned near the rotating shaft 3 without any contact with the upper rotor 5.

To continuously feed the colloidal suspension to the upper side of the upper rotor 5, a tank 10 for preparing a colloidal suspension from microbial cells or enzyme and a colloidal solution, a feed pump 11, a flow rate meter 12 and a flow rate controller 13 are provided. The tank 10 is in such a structure that the colloid solution contained in the tank 10 can be internally or externally heated or cooled, and also stirred by a stirrer provided therein. At the top of the ank 10, an inlet for introducing the colloid solution and microbial cells or enzyme is provided. At the bottom of the tank 10, an outlet for withdrawing a colloidal suspension prepared from the colloidal solution and the microbial cells or the enzyme is provided. In FIG. 1, preparation of the colloidal suspension is carried out in a single tank, but can be made in a plurality of tanks, if necessary. At the bottom of the vessel 1, an outlet 14 for discharging the gel beads accumulated in the container 1 to the outside is provided.

The operation of the present apparatus will be described below.

At first, a predetermined amount of a gelling agent is placed into the vessel 1, and excess gelling agent is withdrawn from the vessel 1 by opening the valve in the liquid discharge pipe 7 to adjust the liquid level of the gelling agent to an appropriate level in the vessel 1. Then, the rotating shaft 3 is vertically moved by the means 8 for vertically moving the rotating shaft to adjust the contact state of the lower rotor 4 with the liquid surface of the gelling agent to an appropriate level in the vessel 1. Then, the motor 2 is started to rotate the lower rotor 4 and the upper rotor 5. By rotation of the lower rotor 4, a surface liquid stream flowing from the center toward the peripheral wall of the vessel 1 can be uniformly formed, and the number of revolution of the lower rotor 4 and the upper rotor 5 is adjusted to an appropriate rpm so as to obtain gel beads having the desired bead size.

On the other hand, a colloidal solution and microbial cells or enzyme are introduced into the tank 10 and stirred by rotation of the stirrer to prepare a colloidal suspension of the microbial cells or enzyme in the colloidal solution. After the surface liquid stream of the gelling agent has been uniformly formed in the vessel 1 by rotation of the lower rotor 4, the colloidal suspension is withdrawn from the tank 10 through the outlet at the bottom of the tank 10 and led to the vessel 1 by the pump 11 while controlling the flow rate of the colloidal suspension to a predetermined one through the flow rate meter 12 and the flow rate controller 13. The colloidal suspension was supplied onto the upper side of the rotating upper rotor 5 through the feed pipe 9. That is, the colloidal suspension supplied to the upper side at a position near the center of the upper rotor 5 moves toward the periphery of the upper rotor 5 by the centrifugal force caused by the rotation and dispersed into droplets by the vanes 18. fixed on the periphery on the upper side of the upper rotor 5. The droplets are made to fall onto the liquid surface of the gelling agent. On the liquid surface of the gelling agent, a surface liquid stream 19 is formed to flow from the center toward the peripheral wall of the vessel 1 by rotation of the lower rotor 4, and the droplets of the colloidal suspension having fallen on the liquid surface of the gelling agent move toward the peripheral wall of the vessel 1 together with the surface liquid stream of the gelling agent and are caught into the gelling agent at the peripheral wall. The droplets caught into the gelling agent are thoroughly contacted with the gelling agent and are changed into gel beads.

Thus, the droplets of colloidal suspension dispersed by the upper rotor 5 move together with the surface liquid stream of the gelling agent in the vessel 1 by rotation of the lower rotor 4 and never stay on the liquid surface of the gelling agent. That is, the droplets of colloidal suspension dispersed by the upper rotor 5 never join with the successively dispersed droplets of colloidal suspension, and the gel beads can be produced continuously. Since gel beads of smaller bead size can be produced at higher rpm of the lower rotor 4 and the upper rotor 5, there is no problem of clogging as encountered when the conventional nozzles are used.

The gel beads thus produced accumulate in the vessel 1. Excessive accumulation of the gel beads in the vessel 1 gives an adverse effect on the production of gel beads, and thus the accumulated gel beads must be occasionally withdrawn to the outside through the outlet provided at the bottom of the vessel 1. Since the gelling agent is consumed during the production of gel beads, it must be supplemented in an amount corresponding to the consumption.

The present invention will be described in detail below, referring to Example.

EXAMPLE

An apparatus for producing gel beads, provided with an upper rotor and a lower rotor at two stages, as shown in FIG. 2, was used. The rotors each had an outer diameter of 10 cm, and the lower rotor had 6 vanes on the lower side of the disk, and the upper rotor had 8 vanes on the upper side of the disk. Number of revolution of the rotors was adjusted by a means for adjusting rpm, provided on a motor. A test colloidal suspension was prepared by suspending 500 g of about 34 wt. % wet microbial cells in 1 l of an aqueous 1.5 wt. % sodium alginate solution. The microbial cells were commercially available bread yeast. An aqueous 1 wt. % $CaCl_2$ solution was used as a gelling agent.

Figure 4:
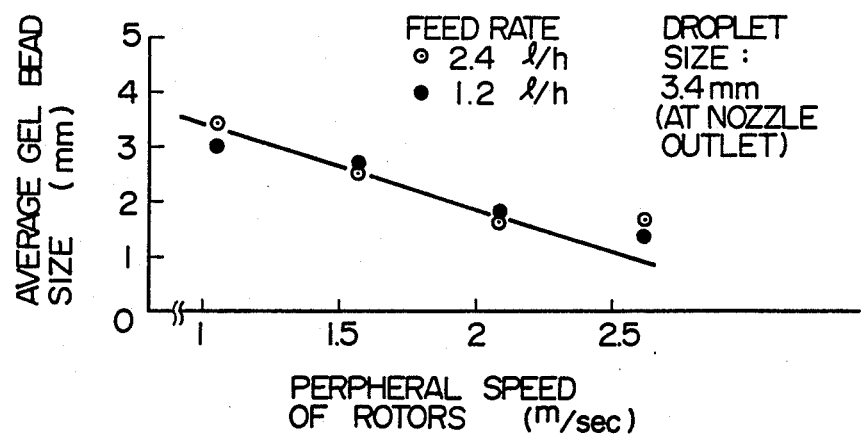
FIG. 4 is a diagram showing a relationship between the peripheral speed of rotors and the average gel bead size.

At first, the rotors were provided at the center in the vessel so that the lower rotor could be brought into contact with the liquid surface of the gelling agent, and the rotors were made to rotate at varied peripheral speeds rauging 1 to 2.6 m/sec to form a surface liquid stream flowing from the center toward the peripheral wall of the vessel on the liquid surface of the gelling agent. Then, the test colloidal suspension was supplied onto the upper side of the upper rotor at a position near the center of the upper rotor by a pump at feed rates of 1.2 l/hr and 2.4 l/hr, thereby dispersing the colloidal suspension into droplets, and the droplets were brought into contact with the surface liquid stream of the gelling agent. It was found that the average bead size of the thus obtained gel beads depended on the peripheral speed of the rotors, as shown in FIG. 4.

The thus obtained gel beads had a bead size distribution. When the rotors were rotated at the peripheral speed of 2.09 m/sec. at the feed rate of 2.4 l/hr, the results as shown in Table 1 were obtained.

TABLE 1

| Bead size | Less than 1 mm | 1–1.5 mm | 1.5–2.0 mm | 2.0–2.5 mm | More than 2.5 mm |
|---|---|---|---|---|---|
| Distribution | 0.165 | 0.421 | 0.174 | 0.174 | 0.066 |

Figure 5:
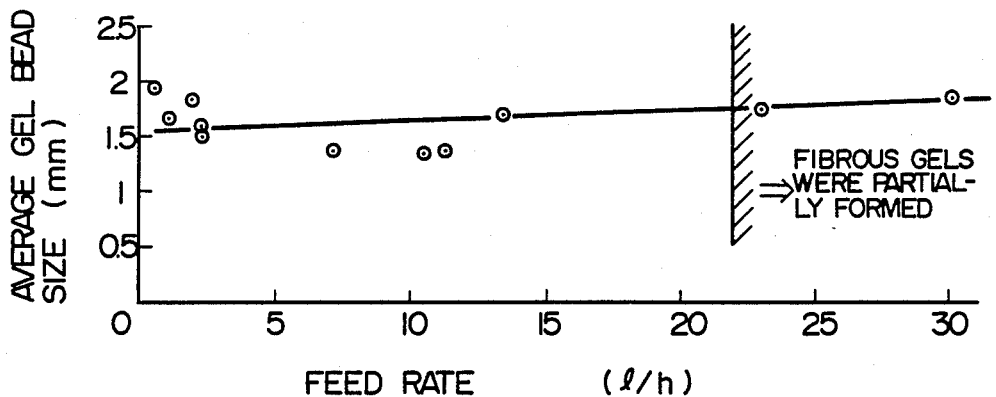
FIG. 5 is a diagram showing a relationship between the feed rate of a colloidal suspension and the average gel bead size.

When the rotors were rotated at the peripheral speed of 20.09 m/sec., and the test colloidal suspension was fed at varied feed rates, results as shown in FIG. 5 were obtained. It was found that gel beads having an average bead size of 1 to 2.0 mm were obtained at a feed rate up to 20 l/hr.

For comparison, the bead size distribution of gel beads obtained by trickling of the same test suspension through a nozzle, 0.5 mm in diameter, without the rotors, is shown in Table 2.

TABLE 2

| Bead size | 1.5–2.5 mm | 2.5–3.5 mm | More than 3.5 mm |
|---|---|---|---|
| Distribution | 0.000 | 1.000 | 0.000 |

As is apparent from Table 2, the bead sizes of the gel beads were as large as about 3.2 mm. Since the droplets were made to fall by gravity from the nozzle in the comparative art, the feed rate was restricted.

In the above Example, the bead size distribution of gel beads was measured by using an image recognition analysis apparatus having a function for measuring bead sizes and a function for operating the bead size distribution. The bead sizes were measured by photographing a 50 to 200 beads by a TV camera and obtaining areas of individual beads from the number of picture elements obtained. Then, the bead sizes were obtained by calculating diameters of circles corresponding to individual areas of beads, provided that the beads are circular. The bead size distribution was obtained by dividing the thus obtained bead sizes with intervals of 0.5 mm and calculating ratios to the total number of beads measured.

The rotors according to other embodiments of the present invention will be given below.

Figure 6:
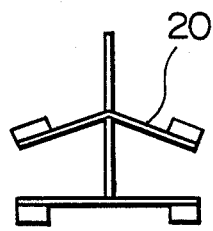
FIGS. 6–8 show structures of rotors according to other embodiments of the present invention.
Figure 7:
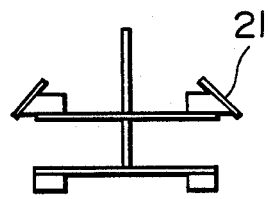
Figure 8:
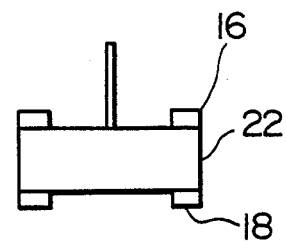

The upper rotor 5 can take such a structure as a conical disk 20, whose both surfaces are inclined downwards, as shown in FIG. 6, or as a conical ring 21 fixed to the vanes 18 at the periphery on the upper side of the disk, as shown in FIG. 7 to make the scattering distance of droplets as short as possible when the colloidal suspension is dispersed into droplets by the rotation. Furthermore, a single rotor 22 having a considerable distance between the upper side and the lower side, provided with vanes 16 and vanes 18 at the pheripheries on the upper side and the lower side of the rotor, respectively, as shown in FIG. 8 can be also used without using the upper rotor and the lower rotor at two stages, as shown in FIG. 2.

In the production of gel beads by dispersing a colloidal suspension of microbial cells or enzyme in a colloidal solution such as an aqueous alginate solution or an aqueous carrageenan solution and contacting the droplets with a gelling agent such as an aqueous calcium chloride solution or a potassium chloride solution, the gel beads can be produced by rotation of rotors in the present invention, and the bead size of the gel beads can be adjusted by controlling the number of revolutions of the rotors. That is, gel heads of smaller bead sizes can be prepared in a mass production scale without any clogging problem as encountered in the conventional production of gel beads by nozzle trickling and without using a large number of nozzles having a small size. The present invention is suitable for gel beads as catalysts to be filled in bioreactors.

What is claimed is:

1. An apparatus for producing gel beads of microbial cells or enzymes enclosed in a gel by dispersing a colloidal suspension of microbial cells or enzymes into a droplet state, and contacting the droplets with a gelling agent, which comprises a vessel containing a liquid gelling agent at a level to provide a liquid surface of the gelling agent within said vessel; an upper rotor and a lower rotor provided coaxially in the vessel, said upper rotor comprising a disk and vanes radially provided at a periphery of an upper side of the disk and the lower rotor comprising a disk and vanes radially provided at a periphery on a lower side of the disk, the lower rotor being provided at a level in contact with the liquid surface of the gelling agent contained in the vessel, the upper rotor and the lower rotor being spaced from each other at a distance sufficient to prevent splashes of the gelling agent caused by rotation of the lower rotor from depositing onto the upper rotor; and a feed pipe for supplying the colloidal suspension onto the upper side of the upper rotor, provided above the upper rotor, whereby rotation of the upper rotor causes droplets of the suspension to fall from the upper side of the upper rotor onto a moving surface of the gelling agent formed by the lower rotor.

2. An apparatus according to claim 1, wherein the upper rotor comprises a conical disk having an upper surface inclined downwards, and the vanes radially provided at the periphery on the upper side of the disk also being inclined downwards.

3. An apparatus according to claim 1, wherein the upper rotor is provided with a conical ring at outer edges of the vanes.

4. An appaatus according to claim 1, wherein the feed pipe is provided at a position near a center of the upper rotor without any contact with the upper side of the upper rotor.

5. An apparatus according to claim 1, wherein the upper rotor and the lower rotor are provided coaxially on a vertically movable, rotating shaft, and the levels of the upper rotor within the vessel and the lower rotor are changeable by vertically moving the rotating shaft.

6. An apparatus according to claim 1, wherein the liquid level of the gelling agent is controlled by a liquid discharge pipe provided at a side wall of the vessel and with a screen at the inlet.

7. An apparatus according to claim 1, further comprising means for maintaining the lower rotor at a level at which the lower rotor is in contact with the liquid surface of the gelling agent within the vessel, said means causing vertical movement of the rotor within the vessel.

8. An apparatus for producing gel beads of microbial cells or enzymes enclosed in a gel by dispersing a colloidal suspension of microbial cells or enzymes into a droplet state and contacting the droplets with a gelling agent, which comprises a vessel containing a liquid gelling agent at a level to provide a liquid surface of the gelling agent within said vessel, a rotor having an upper surface and lower surface arranged within the vessel, the lower surface of the rotor being arranged to contact the liquid surface of the gelling agent contained in the vessel, vanes radially arranged at a periphery of the upper surface and at a periphery of the lower surface of the rotor, the upper and lower surfaces of the rotor being spaced from each other sufficiently to prevent splashes of the liquid gelling agent caused by the lower surface and associated vanes contacting the liquid surface during rotation of the rotor from depositing onto the upper surface of the rotor, and a feed pipe for supplying the colloidal suspension into the upper surface of the rotor being provided above the upper surface of the rotor, whereby rotation of the rotor causes droplets of the suspension to fall from the upper surface onto a moving surface of the gelling agent formed by the lower surface.

9. An apparatus according to claim 8, wherein the rotor comprises a disk rotor.

10. An apparatus according to claim 9, wherein an upper surface of the rotor is inclined downwards.

11. An apparatus according to claim 9, wherein the vanes radially provided at the periphery of the upper surface are provided with a conical ring at an outer edges of the vanes.

12. An apparatus according to claim 8, wherein the feed pipe is provided with a discharge end at a position near a center of the upper surface of the rotor without any contact with the upper surface of the rotor.

13. An apparatus according to claim 8, wherein the liquid level of the gelling agent within the vessel is controlled by a liquid discharge pipe provided at a side wall of the vessel and with a screen over an inlet of the liquid discharge pipe.

14. An apparatus according to claim 8, further comprising means for maintaining the surface of the lower rotor at a level at which the lower surface is in contact with the liquid surface of the gelling agent within the vessel, said means causing vertical movement of the rotor within the vessel.

15. A process for producing gel beads of microbial cells or enzymes contained in a gel, which comprises contacting a lower surface of a rotor having vanes radially arranged at a periphery of the lower surface with a surface of a liquid gelling agent contained in a vessel, rotating the rotor to cause the gelling agent to flow as a stream from a center of the vessel towards a peripheral wall of the vessel, supplying a colloidal suspension of microbial cells or enzymes onto an upper surface of the rotating rotor having vanes radially arranged at a periphery of the upper surface to disperse the colloidal suspension into droplets and to cause the dispersed droplets to fall from the upper surface onto the liquid gelling agent flowing as a stream from the center of the vessel to the peripheral wall of the vessel whereby the dispersed droplets are formed into gel beads, said lower and upper surfaces of the rotor being spaced from each other sufficiently to prevent splashes of the liquid gelling agent caused by the lower surface and associated vanes contacting the liquid surface during rotation of the rotor from depositing onto the upper surface of the rotor.

16. A process according to claim 15, wherein the colloidal suspension includes an aqueous alginate solution or an aqueous carrageenan solution in which the microbial cells or enzymes are suspended, and the gelling agent is an aqueous calcium chloride solution or an aqueous potassium chloride solution.

17. A process according to claim 15, wherein the gel beads are accumulated in a lower portion of the vessel and are periodically discharged from the vessel via a discharge opening located in a lower portion of the vessel.

* * * * *